United States Patent [19]

Holden

[11] Patent Number: Plant 5,457

[45] Date of Patent: Apr. 30, 1985

[54] BLUE SPRUCE TREE "BABY BLUEYES" VARIETY

[76] Inventor: Verl L. Holden, 10374 Hazel Green Rd. NE., Silverton, Oreg. 97381

[21] Appl. No.: 533,277

[22] Filed: Sep. 19, 1983

[51] Int. Cl.[3] ..... A01H 5/12
[52] U.S. Cl. ..... Plt.50
[58] Field of Search ..... Plt./50

*Primary Examiner*—Robert E. Bagwill
*Attorney, Agent, or Firm*—Eugene D. Farley

[57] ABSTRACT

A new and distinct blue spruce tree variety originating as a chance seedling growing among a cultivated group of grafted *Picea pungens* Moerheimi planted in a cultivated nursery area at Silverton, Oreg. The new variety is unique in its upright, semi-dwarf growth habit with early apical dominance; its naturally pyramidal configuration; the delayed spring growth of its dormant buds; and its dense foliage of a sky-grey color. These characteristics make it well suited for a wide range of landscape uses, as well as for live, potted Christmas trees.

4 Drawing Figures

BACKGROUND AND SUMMARY OF THE INVENTION

The present invention relates to a new and distinct variety of blue spruce tree, specifically to the "Baby Blueyes" variety of blue spruce tree.

I discovered the presently described new variety in 1972 as a chance seedling growing in a cultivated group of grafted *Picea pungens* Moerheimi in a cultivated area at my nursery in Silverton, Oreg.

In the propagation of blue spruce trees it is conventional practice to graft a horticultural variety to seedling understock, using a lateral growing bud. The top of the seedling understock is cut off in order to allow the desired variety to grow as a new plant.

It usually is necessary to stake the grafted tree with a steel rod, to which the tree is tied, in order to get a plant having trained apical (terminal) dominance after having been grafted from a lateral growing bud. This procedure is followed in the propagation of all of the commonly grown select blue spruce varieties, such as *Picea pungens* Hoopsi, *Picea pungens* Kosteri, and *Picea pungens* Moerheimi.

This procedure was followed in the case of the plant which developed into my new, presently described variety. The understock was grafted and the top cut off the understock in order to allow the graft to grow.

Seven years passed before I discovered the new plant because it was growing in a group of plants of nearly the same color. During its growth, however, it demonstrated its unique characteristic of terminal dominance at an early age. It was conspicuously different because it did not need to be staked in order to make it grow straight.

My new blue spruce tree variety "Baby Blueyes" is further characterized by the following combination of characteristics:

(a) It is an upright evergreen conifer which assumes a natural, symmetrical pyramidal configuration and which is more dense and slower growing than blue spruce cultivars such as *Picea pungens* Hoopsi, *Picea pungens* Kosteri, *Picea pungens* Moerheimi, *Picea pungens* Bacheri, or *Picea pungens* Thomsoni.

(b) The needles are shorter and closer together than is the case in all of the above named cultivars.

(c) There are more buds on a single branchlet than in the case of the above named cultivars. The buds also are smaller.

(d) The dormant buds start spring growth one to two weeks after the above named cultivars. This helps to assure that the new buds will be less likely to freeze during a late frost.

(e) The foliage is sky-grey and more closely corresponds to The R.H.S. Colour Chart II of The Royal Horticulture Society, London, England Chart Number 449, page 130.

Asexual reproduction of my new variety by cutting and grafting thousands of trees from the mother tree and progeny three times removed has demonstrated that the foregoing unique combination of characteristics, in particular the characteristic terminal dominance at an early age, is fully established and is transmitted to successive generations.

THE DRAWINGS

The accompanying drawings illustrate my new "Baby Blueyes" blue spruce tree and the characteristics of its growth.

FIG. 1 illustrates the attractive, symmetrical, dense, pyramidal growth habit of the mother tree which stands ten feet tall and now is twenty-one years old from seed.

FIG. 2 illustrates the growth habits of a group of seven year old trees propagated asexually from the mother tree. These trees have never been sheared or staked to straighten them.

FIG. 3 illustrates the comparative growth habit and color of the foliage of my new blue spruce tree variety when compared with *Picea pungens* Hoopsi (top) *Picea pungens* Bacheri (right) *Picea pungens* Baby Blueyes (bottom) and *Picea pungens* R.S. Montgomery (left).

FIG. 4 illustrates the comparative growth habit and color of *Picea pungens* Baby Blueyes and *Picea pungens* Hoopsi in two seven year old trees grown side by side in the nursery row.

DETAILED DESCRIPTION OF THE NEW VARIETY

A detailed description of my new "Baby Blueyes" blue spruce tree variety follows, with color terminology being given in accordance with the horticultural colour chart issued by The British Colour Council in collaboration with The Royal Horticultural Society 1941 Edition, Volume 2. The description was made during August, 1983, following the observation of representative plants growing in my nursery at Silverton, Oreg.

Type: Evergreen conifer.

Growth habit: Symmetrical and pyramidal; however taller than wide.

Foliage: Needle shaped, evergreen, rigid, 2–3 cm. long, sky-grey, (chart number 449, page 130) pointed, prickly, developed in a spiraling whorl.

Branches: New branch bark is Spanish orange (chart number 010/1, page 103).

Shape: Substantially similar to *Picea pungens* Glauca when grown from seed.

Color: Sky-grey, (chart number 449, page 130). Color of new growth and of previous years' growth in mid-summer are essentially the same.

Dormant buds: In mid-summer are majolica yellow, (chart number 09/109, page 102).

Fruits: The mother tree has not yet set cones.

Growth rate: Plants seven years from grafting on two three year old root stocks are 36 to 42 inches high with an average base width of 24 to 30 inches. The mother tree is 21 years old and about 10 feet tall. Lateral bud growth is about 5 inches per year while terminal bud growth is about 6 to 8 inches a year.

I claim:

1. A new and distinct variety of blue spruce tree, substantially as herein shown and described, characterized particularly as to novelty by its upright, semi-dwarf growth habit with early apical dominance; its naturally pyramidal configuration; its short, closely spaced needles; its high bud count; the delayed spring growth of its dormant buds; and its dense foliage, sky-grey in color.

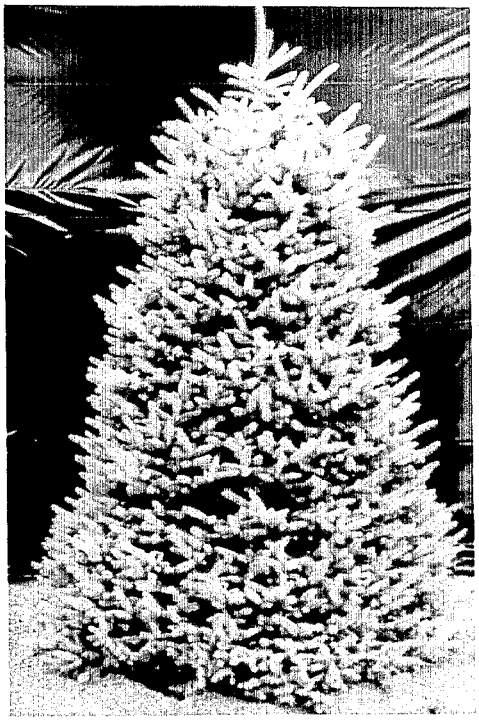
FIG. 1
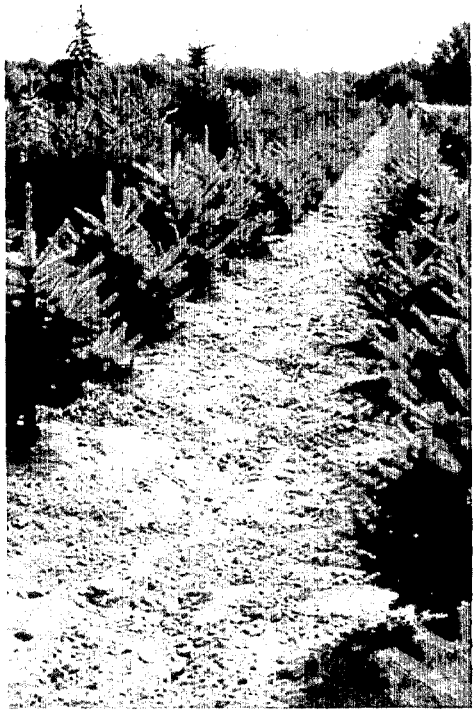
FIG. 2
FIG. 3
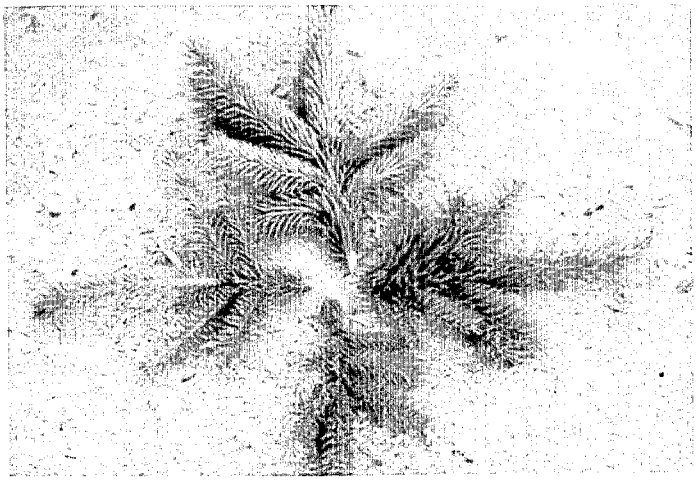
FIG. 4
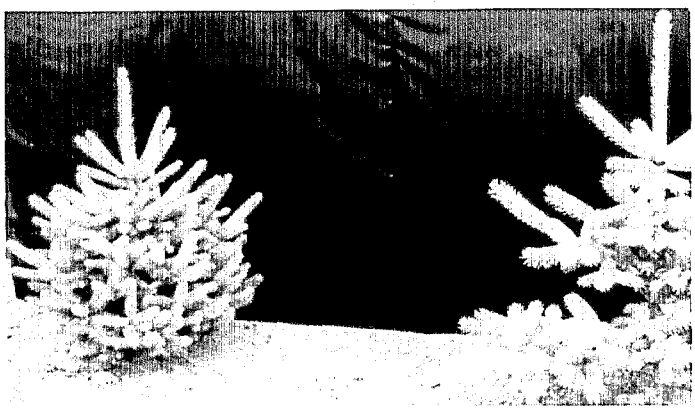

* * * * *